(12) United States Patent
Bhotla et al.

(10) Patent No.: US 9,340,502 B2
(45) Date of Patent: May 17, 2016

(54) METHODS FOR PRODUCING AND PURIFYING 2-ARYL-3,3-BIS(4-HYDROXYARYL)PHTHALIMIDINE COMPOUNDS, THE PURIFIED MONOMERS, AND POLYMERS DERIVED THEREFROM

(71) Applicant: SABIC Innovative Plastics IP B.V., Bergen Op Zoom (NL)

(72) Inventors: Venkata Rama Narayanan Ganapathy Bhotla, Bangalore (IN); Balakrishnan Ganesan, Bangalore (IN); Kishan Gurram, Bangalore (IN); Salkod Parameshwar Mallika, Bangalore (IN); Arun Satyanarayana Kumar, Bangalore (IN); Shubashree Swaminathan, Bangalore (IN)

(73) Assignee: SABIC GLOBAL TECHNOLOGIES B.V. (NL)

( * ) Notice: Subject to any disclaimer, the term of this patent is extended or adjusted under 35 U.S.C. 154(b) by 0 days.

(21) Appl. No.: 14/462,381

(22) Filed: Aug. 18, 2014

(65) Prior Publication Data

US 2014/0357830 A1  Dec. 4, 2014

Related U.S. Application Data

(62) Division of application No. 13/548,934, filed on Jul. 13, 2012, now Pat. No. 8,809,486, which is a division of application No. 12/333,451, filed on Dec. 12, 2008, now Pat. No. 8,247,523.

(51) Int. Cl.

| C08G 73/10 | (2006.01) |
|---|---|
| C07D 209/46 | (2006.01) |
| C08G 64/12 | (2006.01) |
| C08G 73/00 | (2006.01) |
| C08G 73/06 | (2006.01) |

(52) U.S. Cl.
CPC .............. *C07D 209/46* (2013.01); *C08G 64/12* (2013.01)

(58) Field of Classification Search
CPC ....................................................... C08G 73/10
USPC ......... 528/322, 271, 272, 288, 332, 422, 486, 528/488, 503; 548/472
See application file for complete search history.

(56) References Cited

U.S. PATENT DOCUMENTS

| 8,247,523 B2 * | 8/2012 | Bhotla et al. ........... C08G 64/12 528/322 |
|---|---|---|
| 8,809,486 B2 * | 8/2014 | Bhotla et al. ........... C08G 64/12 528/322 |
| 2005/0222334 A1 | 10/2005 | Srinivasan et al. |

| 2005/0288517 A1 | 12/2005 | Rai et al. |
|---|---|---|
| 2007/0010619 A1 | 1/2007 | Chatterjee et al. |
| 2007/0135612 A1 | 6/2007 | Ganesan et al. |

FOREIGN PATENT DOCUMENTS

| GB | 1158606 | 7/1969 |
|---|---|---|
| JP | 6082624 A | 3/1994 |
| WO | WO2008121149 A1 | 10/2008 |
| WO | WO2008121150 A1 | 10/2008 |

OTHER PUBLICATIONS

ASTM Designation: E313-00, "Standard Practice for Calculating Yellowness and Whiteness Indices from Instrumentally Measured Color Coordinates," 2000, pp. 1-5.
Chen, et al., "Synthesis, properties, and gas permeation performance of cardo poly(arylene ether sulfone)s containing phthalimide side groups", Journal of Applied Polymer Science, 106(4) [2007] p. 2808-2616 [Abstract only: XP002568248 Chemical Abstracts.
International Preliminary Report on Patentability, including transmittal, for PCT/IB2009/055672 dated Jun. 23, 2011, 7 pages.
International Search Report, including transmittal, for PCT/IB2009/055672, dated Feb. 24, 2010, 7 pages.
Lin et al., Journal of Polymer Science: Polymer Chemistry Edition, (1981) vol. 19, pp. 2659-2670.
PCT Notification of Transmittal and Int'l Search Report for (P260151PCT) PCT/IB2009/055672, mailed Feb. 24, 2010, 7 pages.
PCT Written Opinion of International Searching Authority for (P260151PCT) PCT/IB2009/055672, mailed Feb. 24, 2010, 7 pages.
Vibhute, et al., "Synthesis and characterization of new cardo polyesters", Journal of Polymer Science, 35(15) (1997) p. 3227-3234 [Abstract only: XP-002568247 Chemical Abstract Service 2 pages].

\* cited by examiner

*Primary Examiner* — Duc Truong
(74) *Attorney, Agent, or Firm* — Cantor Colburn LLP

(57) ABSTRACT

Disclosed herein is a method for producing a purified 2-aryl-3,3-bis(4-hydroxyaryl)phthalimidine of formula (I)

(I)

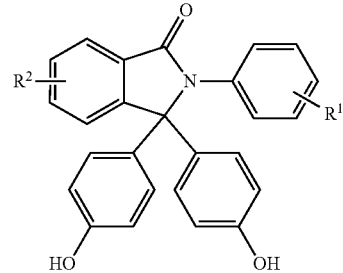

wherein $R^1$ is hydrogen or a $C_{1-25}$ hydrocarbyl group and $R^2$ is a hydrogen, a $C_{1-25}$ hydrocarbyl group, or a halogen, and wherein the method comprises dissolving a crude phthalimidine compound in an aqueous base solution; precipitating the dissolved, crude phthalimidine compound from the aqueous base solution by adding an acid in an amount effective to lower the pH of the solution to 9.0 to 12.0, to provide a semicrude phthalimidine compound; and isolating the semicrude phthalimidine compound from the aqueous base solution, to provide the purified 2-aryl-3,3-bis(4-hydroxyaryl) phthalimidine of formula (I), and having a phenolphthalein compound content of less than 2,500 ppm, based on the weight of the purified 2-aryl-3,3-bis(4-hydroxyaryl)phthalimidine. Subsequent trituration with aqueous methanol and recrystallization from isopropanol can result in product having levels of phenolphthalein derivatives that are not detectable.

9 Claims, No Drawings

METHODS FOR PRODUCING AND PURIFYING 2-ARYL-3,3-BIS(4-HYDROXYARYL)PHTHALIMIDINE COMPOUNDS, THE PURIFIED MONOMERS, AND POLYMERS DERIVED THEREFROM

CROSS-REFERENCE TO RELATED APPLICATIONS

This application is a divisional of U.S. patent application Ser. No. 13/548,934, filed Jul. 13, 2012 now U.S. Pat. No. 8,809,486, which is a divisional of U.S. patent application Ser. No. 12/333,451, filed Dec. 12, 2008 and issued as U.S. Pat. No. 8,247,523, both of which are incorporated herein by reference in their entirety.

BACKGROUND

The present disclosure generally relates to methods for producing and purifying 2-aryl-3,3-bis(4-hydroxyaryl)phthalimidine compounds, the purified compounds, and polycarbonates as well as other polymers derived from the compounds.

3,3-Bis-(4-hydroxy-phenyl)-3H-isobenzofuran-1-one (hereinafter referred to as phenolphthalein) has been used as an aromatic dihydroxy monomer for preparing polycarbonates, which are generally characterized with excellent ductility and high glass transition temperatures. Certain derivatives of phenolphthalein have also been used as aromatic dihydroxy monomers to prepare polycarbonates. For example, polycarbonate homopolymers have been prepared by an interfacial polycondensation method using phosgene and phenolphthalein derivatives such as 3,3-bis(4-hydroxyphenyl)phthalimidine and 2-phenyl-3,3-bis(4-hydroxyphenyl)phthalimidine ("PPPBP").

Lin and Pearce (Journal of Polymer Science: Polymer Chemistry Edition, (1981) Vol. 19, pp. 2659-2670) reported the synthesis of PPPBP by refluxing phenolphthalein and aniline hydrochloride in aniline for 6 hours, followed by recrystallization from ethanol. During this reaction, side products are created which, if not removed, can result in the PPPBP having an unacceptable purity for use as a monomer or as a comonomer in subsequent polymerization reactions. The impurities in the PPPBP include, for example, levels of phenolphthalein or phenolphthalein compounds that can undesirably produce discoloration in the polycarbonates and other polymers derived therefrom. Coloration is not a desirable attribute for many commercial applications. U.S. Pat. No. 5,344,910 discloses that copolymers of PPPBP were found to have poor melt stability resulting in foamy polymer melts and moldings, and discoloration of the polymer during melt processing.

U.S. Publication 2005/0288517 describes a method of purifying 2-aryl-3,3-bis(4-hydroxyaryl)phthalimidine compounds. The technique described in U.S. Publication No. 2005/0288517 achieved phenolphthalein-based impurity levels as low as about 300 ppm based on PPPBP weight. While these levels improved the color and stability of polymers prepared with the purified PPPBP, further improvements in color and stability of polymer made with PPPBP are desirable.

It would therefore be desirable to develop a process for further improving the purity of phenolphthalein derivatives such as 2-aryl-3,3-bis(4-hydroxyaryl)phthalimidine and PPPBP.

BRIEF SUMMARY

This disclosure relates to a method for producing a purified 2-aryl-3,3-bis(4-hydroxyaryl)phthalimidine of formula (I)

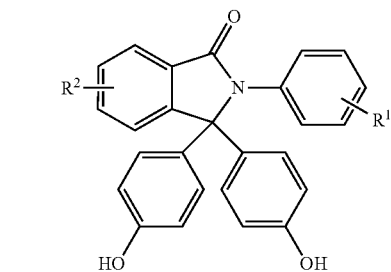

(I)

wherein $R^1$ is hydrogen or a $C_{1-25}$ hydrocarbyl group and $R^2$ is hydrogen, a $C_{1-25}$ hydrocarbyl group, or a halogen, and wherein the method comprises: heating a reaction mixture comprising a phenolphthalein compound of formula (II)

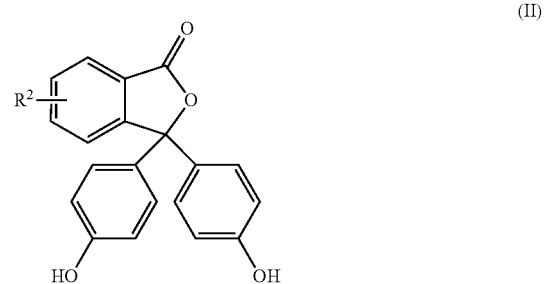

(II)

wherein $R^2$ is hydrogen, a $C_{1-25}$ hydrocarbyl group, or a halogen, a primary aryl amine of formula (III),

(III)

wherein $R^1$ is hydrogen or a $C_{1-25}$ hydrocarbyl group, and an acid catalyst, to form a phthalimidine compound of formula (I); precipitating the phthalimidine compound from the reaction mixture to provide a crude phthalimidine compound; dissolving the crude phthalimidine compound in an aqueous base solution; precipitating the dissolved, crude phthalimidine compound from the aqueous base solution by adding an acid in an amount effective to lower the pH of the solution to 9.0 to 12.0, to provide a semicrude phthalimidine compound; and isolating the semicrude phthalimidine compound from the aqueous base solution, to provide the purified 2-aryl-3,3-bis(4-hydroxyaryl)phthalimidine of formula (I), and having a phenolphthalein compound content of less than 2,500 ppm, based on the weight of the purified 2-aryl-3,3-bis(4-hydroxyaryl)phthalimidine.

In another embodiment, a method for producing a highly purified 2-aryl-3,3-bis(4-hydroxyaryl)phthalimidine of formula (I) comprises: heating a reaction mixture comprising a phenolphthalein compound of formula (II) a primary aryl amine of formula (III and an acid catalyst, to form a phthalimidine compound of formula (I); precipitating the phthalimidine compound from the reaction mixture to provide a crude phthalimidine compound; dissolving the crude phthalimidine compound in an aqueous solution comprising an alkali metal hydroxide, an alkaline earth hydroxide, or a combination comprising at least one of the foregoing metal hydroxides; precipitating the dissolved, crude phthalimidine compound from the aqueous base solution by adding a mineral acid in an amount effective to lower the pH of the solution to 9.0 to 12.0, to provide a semicrude phthalimidine compound; and isolating the semicrude phthalimidine compound from the aqueous base solution, washing the isolated phthalimidine compound with dilute acid, then with water, and drying the washed phthalimidine compound to provide a purified phthalimidine compound of formula (I); triturating the purified phthalimidine compound of formula (I) with an aqueous $C_{1-3}$ alcohol to provide a triturated phthalimidine compound; and washing the triturated phthalimidine compound with aqueous alcohol, then hot water preheated to a temperature of 60 to 80° C.; and drying the washed phthalimidine compound to provide the highly purified 2-aryl-3,3-bis(4-hydroxyaryl)phthalimidine of formula (I), having a phenolphthalein compound content of less than 100 ppm, based on the weight of the 2-aryl-3,3-bis(4-hydroxyaryl)phthalimidine.

In still another embodiment, a method for producing a purified 2-aryl-3,3-bis(4-hydroxyaryl)phthalimidine of formula (I) comprises: heating a reaction mixture comprising a phenolphthalein compound of formula (II), a primary aryl amine of formula (III), and an acid catalyst, to form a phthalimidine compound of formula (I); precipitating the phthalimidine compound from the reaction mixture to provide a crude phthalimidine compound; dissolving the crude phthalimidine compound in an aqueous base solution; precipitating the dissolved, crude phthalimidine compound from the aqueous base solution by adding an acid in an amount effective to lower the pH of the solution to 1.0 to less than 9.0, to provide a semicrude phthalimidine compound; isolating the semicrude phthalimidine compound from the aqueous base solution, to provide the 2-aryl-3,3-bis(4-hydroxyaryl)phthalimidine of formula (I); and sequentially triturating the purified phthalimidine of formula (I) at least twice with an aqueous methanol solution to provide a highly purified 2-aryl-3,3-bis (4-hydroxyaryl)phthalimidine of formula (I), having a phenolphthalein compound content of less than 200 ppm, based on the weight of the 2-aryl-3,3-bis(4-hydroxyaryl)phthalimidine.

This disclosure also relates to purified 2-aryl-3,3-bis(4-hydroxyaryl)phthalimidine compounds produced by the disclosed method.

Also disclosed are polycarbonates and other polymers prepared from the purified 2-aryl-3,3-bis(4-hydroxyaryl)phthalimidine compounds produced by the disclosed method.

The above described and other features are exemplified by the following detailed description.

DETAILED DESCRIPTION

The present disclosure is generally directed to producing and purifying phenolphthalein derivatives, in particular 2-aryl-3,3-bis(4-hydroxyaryl)phthalimidine compounds, which are suitable for use as monomers and/or comonomers for preparing polycarbonates and other polymers. The method generally involves dissolving a crude aryl-3,3-bis(4-hydroxyaryl)phthalimidine compound containing a phenolphthalein contaminant in a basic aqueous solution. A semicrude product is then precipitated from the solution by adding a concentrated acid to achieve a pH from 9.0 to 12.0. The semicrude product is then filtered, washed, and dried to provide a semicrude solid product having a phenolphthalein-based impurity level of less than 2,500 ppm. At least one aqueous methanol trituration may be performed on the semicrude product to give a purified 2-aryl-3,3-bis(4-hydroxyaryl)phthalimidine compound. Typically, the amount of residual phenolphthalein-based impurity in the purified phthalimidine compound is less than 100 ppm, based on the weight of the purified phthalimidine compound. Subsequent triturations with aqueous methanol and recrystallization from isopropanol can produce very highly purified phthalimidine compounds having phenolphthalein-based impurities that are not detectable by high pressure liquid chromatography (HPLC) methods.

The 2-aryl-3,3-bis(4-hydroxyaryl)phthalimidine compounds produced in accordance with these methods can be used in the manufacture of polycarbonates and other polymers having improved properties, such as lower visual coloration and a higher weight average molecular weight. The 2-aryl-3,3-bis(4-hydroxyaryl)phthalimidine compounds can further have higher degradation temperatures, and/or reduced color upon heating.

The 2-aryl-3,3-bis(4-hydroxyaryl)phthalimidine compounds produced in accordance with this disclosure are of formula (I):

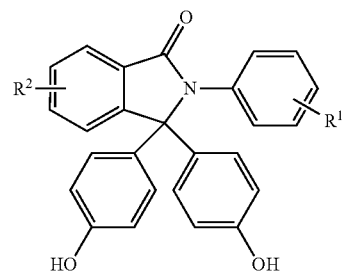

(I)

wherein $R^1$ is hydrogen or a $C_{1-25}$ hydrocarbyl group, and $R^2$ is hydrogen, a $C_{1-25}$ hydrocarbyl group, or a halogen. In one embodiment, $R^1$ is hydrogen, a phenyl, or a $C_{1-3}$ alkyl group, and $R^2$ is hydrogen, a $C_{1-3}$ alkyl group, or a halogen.

The 2-aryl-3,3-bis(4-hydroxyaryl)phthalimidine of formula (I) can be prepared by the reaction of a primary aryl amine, e.g., an aniline of formula (III):

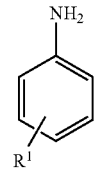

(III)

wherein $R^1$ is as defined above; with a phenolphthalein compound of formula (II):

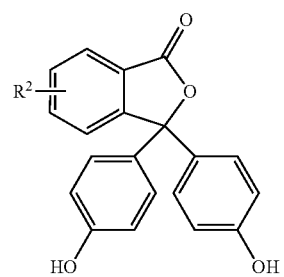

(II)

wherein $R^2$ is as defined above. An acid catalyst is generally used to facilitate formation of the phthalimidine compound.

Exemplary acid catalysts include amine salts of mineral acids. Examples of suitable amines for forming the acid catalysts include primary, secondary, and tertiary amines having any combination of aliphatic and aromatic groups bonded to the amine nitrogen. The mineral acids used for preparing the amine salts can be present in a fluid phase, for example, in a gaseous phase or in a liquid phase or in a combination of the gaseous and liquid phases. Non-limiting examples of mineral acids include hydrogen chloride liquid, hydrogen chloride gas, sulfuric acid, nitric acid, and the like.

Exemplary amine salt catalysts include primary, secondary, and tertiary amine hydrochlorides. In one embodiment, the acid catalyst is introduced as a pre-formed salt of an amine and a mineral acid into the reactor. In another embodiment, the acid catalyst is generated in the reactor by first charging the amine into the reactor, and then adding about ⅓ to about 1 part by weight of an appropriate mineral acid to phenolphthalein compound. In another embodiment, the acid catalyst is generated in the reactor by first charging the amine and an appropriate mineral acid into the reactor, and then adding the phenolphthalein compound. In still another embodiment, about 0.1 parts to about 0.3 parts by weight of hydrogen chloride gas is introduced into a reactor charged with the amine to form an appropriate amount of the amine hydrochloride catalyst. More hydrochloric acid or more hydrogen chloride gas can also used, but is generally not required. A solvent can optionally be used to initially form the amine hydrochloride from the primary hydrocarbyl amine. The solvent can then be removed (if desired), and the amine catalyst, e.g., an aryl amine salt, can be added to the reaction mixture.

The reaction of the aryl amine of formula (III) with the phenolphthalein compound of formula (II) proceeds by a condensation reaction to form the desired phenolphthalein derivative, e.g., the phthalimidine compound of formula (I). An excess of the aryl amine over the phenolphthalein compound can be used to keep the reaction proceeding in a forward direction. The condensation reaction can occur at a temperature of 130° C. to 180° C., specifically at a temperature of 135° C. to 170° C., more specifically at a temperature of 135° C. to 160° C. The reaction can be conducted for 5 to 60 hours, more specifically for 40 to 50 hours.

By way of example, the phenolphthalein compound of formula (II) (wherein $R^2$ is H and $R^1$ is phenyl) was reacted with aniline (formula (III) wherein $R^1$ is H) in the presence of aniline hydrochloride as the acid catalyst to form 2-phenyl-3,3-bis(4-hydroxyphenyl)phthalimidine, shown in formula (IV):

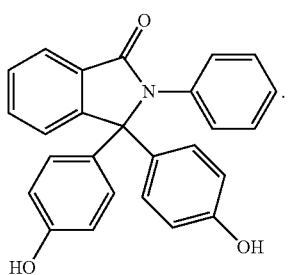

(IV)

In one embodiment, the reaction is conducted at 135° C. to 150° C. over a period from 40 to 50 hours. Water can be removed from the reaction mixture, for example by using an apparatus such as a Dean-Stark apparatus. The so-formed PPPBP can be produced at high yield (70% to 90%).

The PPPBP (or other phthalimidine compounds of formula (I)) can be separated from the reaction mixture by precipitation, for example by pouring the reaction mixture into an antisolvent for the phthalimidine compound such as water. For example, the reaction mixture can be stirred into an acidic aqueous solution or into a mixture of ice and a first concentrated acid to precipitate a crude phthalimidine compound. The crude phthalimidine compound is then isolated, for example by filtration and washing with water. The first acid is not limited and includes hydrochloric acid, sulfuric acid, sulfurous acid, phosphoric acid, and nitric acid. Typically 3 to 9 molar acid is utilized. The crude phthalimidine compound typically contains the phenolphthalein compound in an amount of about 0.35 to about 1.00 weight percent (wt. %), although this amount can vary greatly depending on the reactants and reactant conditions.

The crude phthalimidine compound is then dissolved in an aqueous base solution. The aqueous base can be an alkali metal or alkaline earth metal hydroxide, carbonate, or bicarbonate. Typically, an aqueous sodium hydroxide solution is utilized. The aqueous base solution can contain from 1 to 50% (w/v) of the base. A sufficient amount is used to provide an aqueous base solution containing the crude phthalimidine compound having a pH of greater than 12, specifically greater than 14.

Optionally, the aqueous base solution containing the crude phthalimidine compound is then treated with a solid adsorbent that can remove color-forming species present in the solution. In one embodiment, a commercially available activated carbon is used. Treatment with the activated carbon removes color-forming species present in the solution. Exemplary activated carbons include, but are not intended to be limited to, the NORIT series of activated carbon available from Norit Corporation, and those activated carbons commercially available from E. Merck Company.

In addition to functioning as a decolorizing agent, the activated carbon treatment also aids in selectively adsorbing the 2-aryl-3-{(4-hydroxyaryl)(2-hydroxyaryl)}phthalimidine isomeric impurity, as well as any 2-aryl-3-{(4-hydroxyaryl)(4-aminoaryl)}phthalimidine isomeric impurities. Thus, one method for purifying a crude 2-aryl-3,3-bis(4-hydroxyaryl)phthalimidine compound comprises contacting an aqueous base solution of the crude phthalimidine compound with the activated carbon, removing the activated carbon (e.g., by centrifugation or filtration) to provide treated aqueous base solution containing the crude phthalimidine compound. This treated aqueous base solution can again be treated in the same manner, if desired, to provide further reductions in the levels of the 2-aryl-3-{(4-hydroxyaryl)(2-hydroxyaryl)}phthalimidine impurity and any 2-aryl-3-{(4-hydroxyaryl)(4-aminoaryl)}phthalimidine isomeric impurities.

A second concentrated acid is then added to the aqueous base solution (or treated aqueous base solution) containing the crude product. The second concentrated acid can be the same as those above for the first concentrated acid. In one embodiment, a mineral acid (specifically hydrochloric acid) is used. In one embodiment, the acid is added in an amount and over a period of time sufficient to provide a solution pH of 1.0 to 12.0. However, it has been found that even higher ultimate purities can be obtained when the acid is added in an amount and over a period of time sufficient to provide a solution pH of 9.0 to 12.0, specifically 9.0 to 11.0, more specifically 9.5 to 10.5. Upon adjustment of the pH, a semi-crude phthalimidine compound precipitates from the solution. It is also observed that the solution/slurry changes from a bright pink to a light pink. It is often advantageous to hold the slurry at the final pH for a period of time, for example, the slurry can be stirred for 1 to 3 hours at room temperature.

The semicrude phthalimidine compound is then isolated from the slurry, for example filtered and washed with dilute acid. The dilute acid can be any of the acids listed above with a concentration from 2 to 6 molar. The semicrude phthalimidine compound can then be washed with water and dried. Drying temperatures can range from 60° C. to 120° C., specifically 67 to 100° C. Drying can occur under vacuum.

When precipitation is carried out at a relatively lower pH, i.e., of 1.0 to less than 9.0, the semicrude phthalimidine compound comprises about 0.4000 to 0.7000 wt. % (4,000 to 7,000 ppm) of phenolphthalein compound, specifically about 4,000 to about 6,000 ppm of phenolphthalein compound. The yield of phthalimidine compound is typically about 70% to about 98%, based on the weight of the crude phthalimidine compound.

When precipitation is carried out a pH of 9.0 to 12.0, the semicrude phthalimidine compound has a purity from 98.5 to 99.3 wt. %, and comprises less than about 0.2500 wt. % (2,500 ppm), specifically about 1,000 to about 2,000 ppm of phenolphthalein compound. The yield of phthalimidine compound is typically about 70% to about 98%, based on the weight of the crude phthalimidine compound.

To obtain a purified phthalimidine compound, at least one trituration is performed on the semicrude product. Trituration is conducted using aqueous methanol, in particular a solution comprising 5% to 20% by volume water and 80 to 95% by volume methanol. In one embodiment, trituration is conducted at an elevated temperature that is below the boiling point of the aqueous methanol, for example 45° C. to 90° C., more specifically 50° C. to 80° C. Trituration is conducted for a time effective to decrease the amount of phenolphthalein compound impurities, for example for 5 minutes to 5 hours, more specifically 30 minutes to 2 hours.

The triturated phthalimidine compound is isolated from the aqueous methanol, for example by filtration. In one embodiment the isolated phthalimidine compound is washed with hot water (e.g., water preheated to a temperature of 40° C. to 95°). The washed phthalimidine compound can then be dried, optionally under vacuum at a temperature of e.g., 100° C. to 120° C., to form a purified 2-aryl-3,3-bis(4-hydroxyaryl)phthalimidine compound. When the semicrude phthalimidine compound obtained by precipitation at a pH of 1.0 to less than 9.0 is used, the purified phthalimidine compound has a phenolphthalein compound content of about 400 to 700 ppm. When the semicrude phthalimidine compound obtained by precipitation at a pH of 9.5 to 12.0 is used, the yield of the purified phthalimidine compound, based on the weight of the phenolphthalein compound is typically from 68 to 98%, specifically from 90 to 95%, and the purified phthalimidine compound has a phenolphthalein compound content of less than 100 ppm, specifically about 20 to about 100 ppm. Purified phthalimidine compounds obtained by this process (precipitation at a pH of 9.5 to 12.0, followed by a single methanol trituration) can be used directly to produce polymers having low color.

The purified phthalimidine compound can be triturated a second time to provide a highly purified phthalimidine compound. When the semicrude phthalimidine compound obtained by precipitation at a pH of 1.0 to less than 9.5 is used, the highly purified phthalimidine compound has a phenolphthalein compound content of less than 200 ppm, specifically about 100 to 200 ppm. When the semicrude phthalimidine compound obtained by precipitation at a pH of 9.5 to 12.0 is used, the highly purified phthalimidine compound has a phenolphthalein content of less than 50 ppm, specifically 10 to 50 ppm. The trituration is conducted as described above, using an aqueous methanol solution. Optionally, the product isolated from the second trituration is also washed with aqueous methanol followed by hot water as described above, and dried. The yield of the highly purified phthalimidine compound can be from 70 to 85 wt. %, based on the weight of the semicrude phthalimidine compound.

If a very highly purified phthalimidine compound is desired, the highly purified phthalimidine compound can be further recrystallized from a suitable solvent, for example isopropanol. When the semicrude phthalimidine compound obtained by precipitation at a pH of 9.0 to less than 12.0 is used, the very highly purified phthalimidine compound has a phenolphthalein compound content that is not detectable by the HPLC method described in the experimental section below.

In a specific embodiment of the process described herein, PPPBP (or other phthalimidine compound of formula (I)) is synthesized as described above, than separated from the reaction mixture by precipitation, for example by pouring the reaction mixture into an antisolvent for the phthalimidine compound such as water. For example, the reaction mixture can be stirred into an acidic aqueous solution or into a mixture of ice and a first concentrated acid to precipitate a crude phthalimidine compound. The crude phthalimidine compound is then isolated by filtration and washing with water. The crude phthalimidine compound is then dissolved in an aqueous solution containing an alkali metal hydroxide, an alkaline earth hydroxide, or a combination comprising at least one of the foregoing metal hydroxides. Next the dissolved, crude phthalimidine compound is precipitated from the aqueous base solution by adding a mineral acid in an amount effective to lower the pH of the solution to 9.0 to 12.0, to provide a semicrude phthalimidine compound. The semicrude phthalimidine compound is then isolated from the aqueous base solution and the isolated phthalimidine compound is washed with dilute acid, then with water, and followed by drying to provide a purified phthalimidine compound of formula (I). The purified phthalimidine compound of formula (I) is then triturated with aqueous methanol to provide a triturated phthalimidine compound. The triturated phthalimidine compound is washed with aqueous methanol as described above, then hot water (preheated to a temperature of 60 to 80° C.) and the washed phthalimidine compound is dried to provide the highly purified 2-aryl-3,3-bis(4-hydroxyaryl)phthalimidine of formula (I), having a phenolphthalein compound content of less than 100 ppm, based on the weight of the 2-aryl-3,3-bis(4-hydroxyaryl)phthalimidine. Optionally a second trituration can be performed, optionally followed by recrystallization from a suitable solvent such as isopropanol as described above.

For convenience, the phenolphthalein (PP) content and typical yields of PPPBP purified in accordance with the above-described procedures is set forth in the Table below.

| Stage | Procedure | PP (ppm) | Yield (%) |
|---|---|---|---|
| Crude PPPBP | Precipitated from reaction | 5000-7000 | — |
| Semicrude PPPBP | After precipitation at pH = 1-2 | 4000-6000 | 98% |
| Semicrude PPPBP | After precipitation at pH = 3-4 | 5000-7000 | 98% |
| Semicrude PPPBP | After precipitation at pH = 9.5 | <2500 | 97%* |
| Purified PPPBP | After precipitation at pH = 1-2, one MeOH trituration | 400-700 | 85-93% |

| Stage | Procedure | PP (ppm) | Yield (%) |
|---|---|---|---|
| Purified PPPBP | After precipitation at pH = 9.5, one MeOH trituration | <100 | 94-95%* |
| Highly purified PPPBP | After precipitation at pH = 1-2, two MeOH triturations | 100-200 | 70-85% |
| Highly purified PPPBP | After precipitation at pH = 9.5, two MeOH triturations | <50 | 78-85%* |
| Very highly purified PPPBP | After precipitation at pH = 9.5, two MeOH triturations, one isopropanol trituration | N.D. | — |

*Based on the weight of the semicrude PPPBP
N.D.—not detectable

The 2-aryl-3,3-bis(4-hydroxyaryl)phthalimidines, including the exemplary 2-phenyl-3,3-bis(4-hydroxyphenyl)phthalimidine (PPPBP), are commercially valuable monomers or comonomers for producing a variety of polymers formed by reactions of the phenolic OH groups of the 2-aryl-3,3-bis (4-hydroxyaryl)phthalimidines. Exemplary polymers that can be produced include homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, ester carbonate, and carbonate repeat units, and a polyetherketone. An example of a copolymer comprising aromatic ester, estercarbonate, and carbonate repeat units is the copolymer produced by the reaction of a hydroxy-terminated polyester, such as the product of reaction of isophthaloyl chloride and terephthaloyl chloride with resorcinol, with phosgene and an aromatic dihydroxy compound, such as bisphenol A.

In one embodiment, polycarbonates having low color properties are synthesized, wherein the polycarbonates include structural units of formula (V):

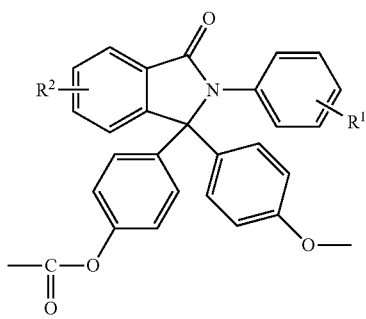

(V)

which are derived from a 2-aryl-3,3-bis(4-hydroxyaryl)phthalimidine of formula (I), wherein $R^1$ and $R^2$ are as described previously; and the C=O structural units are derived from a C=O donor such as a carbonic acid diester in a melt transesterification process, or phosgene in an interfacial process.

Specific polycarbonates are copolycarbonates having structural units derived from a phthalimidine compound of formula (I) and a dihydroxy compound of the formula HO—$R^1$—OH, in particular of formula (VI)

$$\text{HO-}A^1\text{-}Y^1\text{-}A^2\text{-OH} \tag{VI}$$

wherein each of $A^1$ and $A^2$ is a monocyclic divalent aromatic group and $Y^1$ is a single bond or a bridging group having one or more atoms that separate $A^1$ from $A^2$. In an exemplary embodiment, one atom separates $A^1$ from $A^2$. Specifically, each $R^1$ can be derived from a dihydroxy aromatic compound of formula (VII):

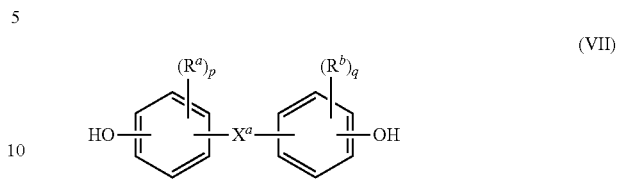

(VII)

wherein $R^a$ and $R^b$ each represent a halogen or $C_{1-12}$ alkyl group and can be the same or different; and p and q are each independently integers of 0 to 4. $X^a$ represents a single bond or a bridging group connecting the two hydroxy-substituted aromatic groups, where the single bond or the bridging group and the hydroxy substituent of each $C_6$ arylene group are disposed ortho, meta, or para (specifically para) to each other on the $C_6$ arylene group. In an embodiment, the bridging group $X^a$ is —O—, —S—, —S(O)—, —S(O)$_2$—, —C(O)—, or a $C_{1-18}$ organic group. The $C_{1-18}$ organic group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic group. In one embodiment, p and q is each 1, and $R^a$ and $R^b$ are each a $C_{1-3}$ alkyl group, specifically methyl, disposed meta to the hydroxy group on each arylene group.

In an embodiment, $X^a$ is a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Exemplary groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene. In another embodiment, $X^a$ is a $C_{1-18}$ alkylene group, a $C_{3-18}$ cycloalkylene group, a fused $C_{6-18}$ cycloalkylene group, or a group of the formula —$B^1$—W—$B^2$— wherein $B^1$ and $B^2$ are the same or different $C_{1-6}$ alkylene group and W is a $C_{3-12}$ cycloalkylidene group or a $C_{6-16}$ arylene group.

Other useful aromatic dihydroxy compounds of the formula HO—$R^1$—OH include compounds of formula (VIII):

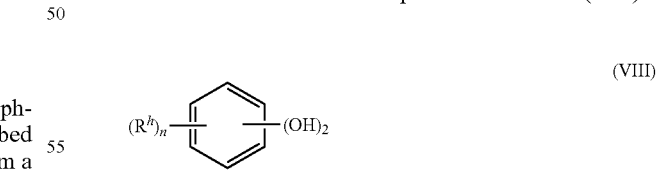

(VIII)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen is usually bromine.

Some illustrative examples of specific aromatic dihydroxy compounds include the following: 4,4'-dihydroxybiphenyl, 1,6-dihydroxynaphthalene, 2,6-dihydroxynaphthalene, bis (4-hydroxyphenyl)methane, bis(4-hydroxyphenyl)diphenylmethane, bis(4-hydroxyphenyl)-1-naphthylmethane, 1,2-bis (4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula (VII) include 1,1-bis(4-hydroxyphenyl)methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-2-methylphenyl)propane, 1,1-bis(4-hydroxy-t-butylphenyl)propane, 3,3-bis(4-hydroxyphenyl)phthalimidine, and 1,1-bis(4-hydroxy-3-methylphenyl)cyclohexane (DMBPC). Combinations comprising at least one of the foregoing dihydroxy compounds can also be used. In one specific embodiment, the polycarbonate is a linear homopolymer derived from bisphenol A, in which each of $A^1$ and $A^2$ is p-phenylene and $Y^1$ is isopropylidene in formula (3).

Exemplary carbonic acid diesters useful in the formation of the polycarbonates in a melt transesterification process are of formula (IX):

$$(ZO)_2C=O \quad (IX)$$

wherein each Z is independently an unsubstituted or substituted $C_{1-12}$ alkyl radical, or an unsubstituted or substituted $C_{6-22}$ aryl radical. Examples of carbonic acid diesters include, but are not limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations thereof. Diphenyl carbonate is widely used as a carbonic acid diester due to its low cost and ready availability on a commercial scale. Use of activated aromatic carbonates that are more reactive than diphenyl carbonate is also contemplated. Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate. Unsymmetrical combinations of these structures are also contemplated. Exemplary ester-substituted diaryl carbonates include, but are not limited to, bis(methylsalicyl)carbonate (CAS Registry No. 82091-12-1) (also known as BMSC or bis(o-methoxycarbonylphenyl)carbonate), bis(ethyl salicyl)carbonate, bis(propyl salicyl)carbonate, bis(butylsalicyl)carbonate, bis(benzyl salicyl)carbonate, bis(methyl 4-chlorosalicyl)carbonate, and the like. In one embodiment, BMSC is used in the melt transesterification process.

The melt transesterification process is generally carried out by combining a catalyst, the carbonic acid diester of formula (IX), the phthalimidine compound of formula (I), and optionally a dihydroxy comonomer; and mixing the reaction mixture under reactive conditions for a time period effective to produce the polycarbonate product. Exemplary melt transesterification catalysts include alkali metal compounds, alkaline earth metal compounds, tetraorganoammonium compounds, tetraorganophosphonium compounds, and combinations comprising at least one of the foregoing catalysts. Specific examples of alkali metal compounds or alkaline earth metal compounds include, but are not limited to, sodium hydroxide, potassium hydroxide, calcium hydroxide, magnesium hydroxide, sodium bicarbonate, potassium bicarbonate, sodium carbonate, potassium carbonate, lithium carbonate, sodium acetate, potassium acetate, sodium stearate, potassium stearate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like. Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide, and the like.

In one embodiment, the catalyst is tetrabutylphosphonium acetate. In an alternative embodiment, the catalyst comprises a mixture of an alkali metal salt or alkaline earth metal salt with at least one quaternary ammonium compound, at least one quaternary phosphonium compound, or a mixture thereof. For example, the catalyst can be a mixture of sodium hydroxide and tetrabutylphosphonium acetate. In another embodiment, the catalyst is a mixture of sodium hydroxide and tetramethylammonium hydroxide. In yet another embodiment, the catalyst comprises the salt of a non-volatile inorganic acid, for example alkali metal salts of phosphites; alkaline earth metal salts of phosphites; alkali metal salts of phosphates; and alkaline earth metal salts of phosphates, including but not limited to $NaH_2PO_3$, $NaH_2PO_4$, $Na_2H_2PO_3$, $KH_2PO_4$, $CsH_2PO_4$, $Cs_2H_2PO_4$, or a mixture thereof. In one embodiment, the transesterification catalyst comprises both the salt of a non-volatile acid and a basic co-catalyst such as an alkali metal hydroxide. This concept is exemplified by the use of a combination of $NaH_2PO_4$ and sodium hydroxide as the transesterification catalyst.

Any of the catalysts disclosed above can be used as combinations of two or more substances. Moreover, the catalyst can be added in a variety of forms. For example, the catalyst can be added as a solid as a powder, or it can be dissolved in a solvent, for example, in water or alcohol. The total catalyst composition can be about $1 \times 10^{-7}$ to about $2 \times 10^{-3}$ moles, and in other embodiments, about $1 \times 10^{-6}$ to about $4 \times 10^{-4}$ moles, for each mole of the combination of, for example, the purified PPPBP and the aromatic dihydroxy comonomer.

The progress of the polymerization reaction can be monitored by measuring the melt viscosity or the weight average molecular weight of the reaction mixture using techniques known in the art such as gel permeation chromatography. These properties can be measured by taking discreet samples or can be measured on-line. After the desired melt viscosity and/or molecular weight is reached, the final polycarbonate product can be isolated from the reactor in a solid or molten form. The method of making polycarbonates as described in the preceding sections can be made in a batch or a continuous process.

In one embodiment, the melt-polymerized polycarbonate is prepared in an extruder in the presence of one or more catalysts. The reactants for the polymerization reaction can be fed to the extruder in powder or molten form. In one embodiment, the reactants are dry blended prior to addition to the extruder. The extruder can be equipped with pressure reducing devices (e.g., vents) that serve to remove the activated phenol byproduct and thus drive the polymerization reaction toward completion. The molecular weight of the polycarbonate product can be manipulated by controlling, among other factors, the feed rate of the reactants, the type of extruder, the extruder screw design and configuration, the residence time in the extruder, the reaction temperature, and the pressure reducing techniques present on the extruder. The molecular weight of the polycarbonate product can also depend upon the structures of the reactants and the catalyst employed. Many different screw designs and extruder configurations are commercially available that use single screws, double screws, vents, back flight and forward flight zones, seals, sidestreams, and sizes.

Alternatively, the polycarbonates can be prepared by an interfacial polymerization process. Although the reaction conditions for interfacial polymerization can vary, an exemplary process generally involves dissolving or dispersing a dihydric phenol reactant in aqueous caustic soda or potash, adding the resulting mixture to a water-immiscible solvent medium, and contacting the reactants with a carbonate precursor in the presence of a catalyst such as triethylamine and/or a phase transfer catalyst, under controlled pH conditions, e.g., about 8 to about 12. The most commonly used water immiscible solvents include methylene chloride, 1,2-dichloroethane, chlorobenzene, toluene, and the like.

Exemplary carbonate precursors for interfacial polymerization include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an exemplary embodiment, an interfacial polymerization reaction to form carbonate linkages uses phosgene as a carbonate precursor, and is referred to as a phosgenation reaction.

Among the phase transfer catalysts that can be used for interfacial polymerization are tetraorganoammonium compounds and tetraorganophosphonium compounds of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Exemplary phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cl^-$, $Br^-$, a $C_{1-8}$ alkoxy group or a $C_{6-18}$ aryloxy group. An effective amount of a phase transfer catalyst can be about 0.1 to about 10 wt % based on the weight of bisphenol in the phosgenation mixture. In another embodiment an effective amount of phase transfer catalyst can be about 0.5 to about 2 wt % based on the weight of bisphenol in the phosgenation mixture.

All types of polycarbonate end groups are contemplated as being useful in the polycarbonate composition, provided that such end groups do not significantly adversely affect desired properties of the compositions. Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate. Exemplary chain stoppers include certain mono-phenolic compounds, mono-carboxylic acid chlorides, and/or mono-chloroformates.

The interfacial method described above can be suitably adapted to produce polycarbonates through the intermediate formation of 2-aryl-3,3-bis(4-hydroxyaryl)phthalimidine bischloroformate. This method is sometimes called the bischloroformate polymerization method. In one embodiment, the method comprises reacting a 2-aryl-3,3-bis(4-hydroxyaryl)phthalimidine with phosgene in an organic solvent, and then reacting the bischloroformate either with a 2-aryl-3,3-bis(4-hydroxyaryl)phthalimidine, or an aromatic dihydroxy compound in the presence of an acid acceptor and an aqueous base to form the polycarbonate. The interfacial polymerization method and the bischloroformate polymerization method can be carried in a batch or a continuous mode using one or more reactor systems. To carry out the process in a continuous mode, one or more continuous reactors, such as for example, a tubular reactor can be used. In one embodiment, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one endcapping agent, optionally one or more solvents, and at least one catalyst. The endcapped polycarbonate thus formed is continuously removed from the tubular reactor system.

The processes disclosed herein can advantageously be used to prepare, for example, PPPBP homopolycarbonate and copolycarbonates having a weight average molecular weight (Mw) of about 3,000 to about 150,000 Daltons and a glass transition temperature (Tg) of about 80° C. to about 300° C. The number average molecular weights (Mn) of the homopolycarbonate and copolycarbonates can be from about 1,500 to about 75,000 Daltons.

Polymers comprising structural units derived from the phthalimidine compounds, in particular PPPBP can be used to manufacture polymer blends comprising the polymer and at least one other thermoplastic polymer. The at least one other thermoplastic polymer includes vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, ABS resins, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, tetrafluoroethylene, polycarbonate-polyorganosiloxane block copolymers, copolymers comprising aromatic ester, estercarbonate, and carbonate repeat units, and combinations comprising at least one of the foregoing polymers.

The polymers and polymer blends described hereinabove are valuable for producing articles. In one embodiment, an article comprises a polymer comprising structural units derived from a 2-aryl-3,3-bis(4-hydroxyaryl)phthalimidine of formula (I) prepared by following the process described above.

Polymers, particularly polycarbonate homopolymers and copolymers comprising structural units derived from the high purity 2-aryl-3,3-bis(4-hydroxyaryl)phthalimidine in general, and PPPBP in particular exhibit lower visual coloration. As such, these polycarbonate polymers are useful for producing articles having a number of useful properties, including lower visual color, among others. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmission, of greater than or equal to about 85 percent.

In addition to the polymer, the thermoplastic compositions comprising the polymers can include various additives ordinarily incorporated into polymer compositions of this type, with the proviso that the additive(s) are selected so as to not significantly adversely affect the desired properties of the thermoplastic composition, in particular low color. Such additives can be mixed at a suitable time during the mixing of the components for forming the composition. Exemplary additives include fillers, reinforcing agents, antioxidants, heat stabilizers, light stabilizers, ultraviolet (UV) light stabilizers, plasticizers, lubricants, mold release agents, antistatic agents, colorants such as such as titanium dioxide, carbon black, and organic dyes, surface effect additives, radiation stabilizers, flame retardants, and anti-drip agents. A combination of additives can be used, for example a combination of a heat stabilizer, mold release agent, and ultraviolet light stabilizer. In general, the additives are used in the amounts generally known to be effective. The total amount of additives (other than any impact modifier, filler, or reinforcing agents) is generally 0.01 to 5 wt. %, based on the total weight of the composition.

The methods described herein are further illustrated by the following non-limiting examples.

EXAMPLES

In the following examples, molecular weights were measured by gel permeation chromatography using polystyrene standards.

Glass transition temperatures of the polycarbonates were measured by differential scanning calorimetry by heating the sample at the rate of 10° C. to 20° C. per minute under nitrogen.

Purity of 2-phenyl-3,3-bis(4-hydroxyphenyl)phthalimidine (PPPBP) and phenolphthalein (PP) content were determined by HPLC. HPLC analysis was performed using a solution of about 50 milligrams of the sample dissolved in about 10 milliliters (mL) of methanol. The HPLC instrument was equipped with a C18 (reverse phase) column maintained at a temperature of 40° C., and an ultraviolet detector capable of detecting components at a wavelength of 230 nanometers. A solvent mixture of methanol and water of varying relative proportions was used. The flow rate was maintained at 1 milliliter per minute. Area percent assay was computed from the area value for each peak detected in the chromatogram divided by the total area from all peaks detected. To determine weight percent, calibration curves for PPPBP and PP were first generated. Then the weight percent of a given component in a sample was calculated using these calibration curves. The PP detection limit for the method is 10 ppm.

Heat aging stability of polymers was determined by measuring the number average molecular weight (Mn) and weight average molecular weight (Mw) of the polymers by gel permeation chromatography as described above, initially and after 7 days of aging at 160° C. and 180° C.

YI was determined using a Macbeth Instrument. The APHA of the polymer sample was measured on a 2.5 weight percent (weight/volume) solution in dichloromethane using a Macbeth Instrument. The APHA shift relative to blank (dichloromethane) is given as the APHA for the polymer sample.

Examples A-F

In these examples, a crude PPPBP was purified by precipitation at a range of pH values. To obtain the crude PPPBP, a mixture of PP (100 g, 0.31 moles), aniline (117 g, 1.25 moles), and concentrated aqueous hydrochloric acid (33 ml, 0.34 moles) was heated under reflux at a temperature of about 140° C. to about 145° C. for 45 hours under nitrogen. The resulting dark solution was then stirred into a mixture of water and concentrated HCl. The violet colored, crystalline crude PPPBP product was separated by filtration and washed with water.

Samples of the crude crystals (121 g) were then dissolved in 275 mL of 5% (w/v) sodium hydroxide solution. The solution was treated twice with 12 g of activated carbon, and then filtered. The filtrate was treated by drop-wise addition of concentrated HCl with stirring, until the filtrate achieved the pH indicated in Table 1. The slurry containing PPPBP solids was stirred for one hour after the desired pH was attained. Where possible, the solid phthalimidine compound was then filtered, washed with 5 M HCl, and then washed with water until the water washings were neutral, and dried under vacuum at 110° C. to yield semicrude PPPBP. The pH of the filtrate at which the precipitation was carried out, the wt. % of PP in the semicrude PPPBP, and the percent recovery (based on the weight of the crude PPPBP) is shown in the Table 1.

TABLE 1

| Example | Treatment of Crude PPPBP | % of PP | % Recovery |
|---|---|---|---|
| Crude | — | 0.4516 | NA |
| A* | pH = 12.5 | No solid formed | NA |

TABLE 1-continued

| Example | Treatment of Crude PPPBP | % of PP | % Recovery |
|---|---|---|---|
| B | pH = 11.5 | 0.1122 | 68 |
| C | pH = 10.5 | 0.0693 | 86 |
| D | pH = 10.0 | 0.2300 | 97 |
| E | pH = 9.5 | 0.2069 | 97 |
| F | pH = 1.7 | 0.4304 | 98 |

*Comparative
NA—Not applicable

As can be seen from the data in the Table 1, precipitation of semicrude PPPBP at a filtrate pH from 1.7 to 10.5 provides good recovery. Unexpectedly, precipitation of semicrude PPPBP at a filtrate pH from 9.5 to 10.5 results in both excellent recovery and significant removal of PP impurities from the PPPBP.

Example 1

Preparation of Semicrude PPPBP by Precipitation at pH=9.5

A mixture of PP (50 g), aniline (58.5 g), and concentrated aqueous hydrochloric acid (10 M, 16.4 g) was heated under reflux at a temperature of about 140° C. to about 145° C. for 45 hours under nitrogen, with removal of water using a Dean-Stark apparatus. The resulting dark solution was then stirred into a mixture of ice and concentrated HCl. The violet colored, crystalline crude PPPBP product was separated by filtration and washed with water. At this stage, the crude PPPBP typically has a PP content of 0.5 to 0.7% by weight of the crude PPPBP. In this example, the crude PPPBP had a purity of 99.3139% as determined by HPLC, and a PP content of 0.5378 wt. % (5,378 ppm).

The crude crystals (20 g) were then dissolved in 130 mL of 4% (w/v) sodium hydroxide solution. The solution was treated twice with 2 g each of activated carbon, and then filtered. The filtrate was treated by drop-wise addition of concentrated HCl with stirring. The aqueous base solution changed from a bright pink solution to a pale pink, thick slurry with a pH of 9.5. The slurry was stirred for one hour after the desired pH was attained. The precipitated phthalimidine compound was then filtered, washed with dilute HCl (5 M), and then washed with water until the water washings were neutral, and dried under vacuum at 70° C. The semicrude PPPBP crystalline solid was obtained in a yield of 97.9% based on the crude PPPBP crystals, and had a purity of 99.65%, with a PP content of 0.2095 wt. % (2,095 ppm).

Example 2

Preparation of Purified PPPBP (Single Trituration)

A portion of the semicrude PPPBP product (15 g) of Example 1 was triturated at reflux temperature (70° C.) once for one hour using aqueous methanol (75 mL, 90% MeOH v/v). Trituration was followed by cooling to room temperature, then filtration of the solid PPPBP, which was then washed with 15 mL of aqueous methanol and then 1 mL of hot water (75° C.). The hot water-treated product was dried under vacuum at 110° C. to provide purified PPPBP (14.12 g) having a purity of 99.91% as determined by HPLC and a PP content of 0.0085 wt. % (85 ppm). The yield of the purified product was 94.1%, based on the semicrude PPPBP.

Example 3

Preparation of Highly Purified PPPBP (Double Trituration)

A portion of the semicrude PPPBP (20 g), prepared as described in Example 1 (except that precipitation was carried out at a pH of 1-2), was subjected to two sequential triturations with aqueous methanol. The semicrude PPPBP had a PP content of 0.45149% by weight, based on the semicrude PPPBP. A first trituration with 100 mL of aqueous methanol (90% MeOH v/v) at reflux temperature (70° C.) was followed by cooling to room temperature, filtration of the solid PPPBP, washing with 20 mL of aqueous methanol and suction drying. The suction-dried PPPBP after the first methanol trituration was obtained in a yield of 90.5%, based on the semicrude PPPBP, and had a PP content of 0.05296 wt. %, based on the weight of the suction-dried PPPBP.

This PPPBP was then subjected to a second trituration with aqueous methanol (100 mL, 90% MeOH v/v) at reflux temperature (70° C.). Trituration was followed by cooling to room temperature, then filtration of solid PPPBP, washing with 15 mL of aqueous methanol and 20 mL of hot water (75° C.). The hot water-treated product was dried under vacuum at 110° C. to provide a highly purified PPPBP having a PP content of 0.00127 wt. % (12.7 ppm), based on the weight of the residue. The yield was 91%, based on the suction-dried PPPBP used for the second trituration. The overall recovery of the highly purified PPPBP was 82%, based on the weight of the semicrude PPPBP.

Example 4

Preparation of Very Highly Purified PPPBP (Double Trituration and Crystallization)

Another portion of the semicrude PPPBP (60 g), prepared as described in Example 1, was subjected to two sequential triturations with aqueous methanol (240 mL each), followed by crystallization with aqueous isopropanol (250 mL, 90% isopropanol v/v). After each aqueous methanol trituration, the solid PPPBP was filtered and washed with 60 mL of aqueous methanol and dried by suction. Crystallization with isopropanol was followed by hot water treatment. The hot water-treated product was dried under vacuum at 110° C. to provide a very highly purified PPPBP wherein the PP was not detectable using HPLC as described above. In addition, the product did not give any pink coloration with sodium hydroxide solution. The yield was 74%, based on the weight of the semicrude PPPBP used for the triturations, and the purity of the very highly purified PPPBP was 99.95 wt % by HPLC.

Example 5

Comparative

This example is in accordance with the commercial process for preparing PPPBP as described in U.S. Patent Publication No. 2005/0288517. Accordingly, a mixture of PP (20 g), aniline hydrochloride (20 g), and 60 mL of aniline was heated under reflux at a temperature of about 180 to about 185° C. for 5 hours under nitrogen. The resulting dark solution was then stirred into a mixture of 100 grams of ice and 70 grams of concentrated HCl. The crystalline, violet-colored product was filtered off and washed with water. The crystals were then dissolved in an ice-cold 10% (w/v) sodium hydroxide solution. The solution was treated with 0.2 g active carbon, and then filtered. Upon drop-wise addition of concentrated HCl into the stirred filtrate, the color changed to bright pink, then to a pure white, thick slurry having a pH of 3 to 4. The precipitated PPPBP was then washed to neutral with water and dried under vacuum at 70° C. The semicrude PPPBP crystals had a melting point of 288 to 291° C. The yield was 79%, based on the weight of the starting PP. At this stage, the crystals have a PP content of 5000 to 7000 ppm.

Double crystallization from ethanol, followed by drying the crystals under vacuum at 150° C. yielded a PPPBP product having a PP content of 274 pm. In contrast, a single trituration with aqueous methanol yields PPPBP having a PP content of less than 500 ppm.

Alternatively, the semicrude PPPBP crystals (20 g) are triturated with aqueous methanol (72 mL methanol and 8 mL water) at reflux for one hour, cooled to room temperature, filtered, washed with 20 mL of aqueous methanol, washed with 20 mL of hot water (75° C.), and dried under vacuum for 14 hours at 110° C., to provide a PPPBP product having a PP content of 300 to 350 ppm.

Examples 1A, 1B, 2A, and 3A

The precipitation procedure of Example 1 and the trituration procedures of Examples 2 and 3 were repeated using a semicrude PPPBP containing 0.4516 wt. % of PP. In Example 1A, the precipitation procedure of Example 1 was followed, except that the pH of the solution was adjusted to about 1 to 2. In Example 1B, the precipitation procedure of Example 1 was followed, with the pH of the solution being adjusted to 9.5. In Example 2A, the product of Example 1A (precipitation at pH of about 1 to 2) was purified using the single trituration procedure of Example 2. In Example 3A, the product of Example 1A (precipitation at pH of about 1 to 2) was purified using the double trituration procedure of Example 3.

The wt. % of PP and the yield for each Example is shown in Table 2. The percent yield is based on the weight of semicrude PPPBP.

TABLE 2

| Ex. | Procedure | % PP | % Yield |
|---|---|---|---|
| — | Semicrude PPPBP | 0.4516 | |
| 1A* | After precipitation at pH = about 1-2 | 0.4304 | 98% |
| 1B | After precipitation at pH = 9.5 | 0.2069 | 97% |
| 2A | After precipitation at pH = about 1-2, and one MeOH trituration | 0.05296 | 90.5% |
| 3A | After precipitation at pH = about 1-2, and two MeOH triturations | 0.00127 | 82% |

*Control

As can be seen from the results shown in Table 2, aqueous methanol trituration can be used to remove PP from semicrude PPPBP containing high amounts of PP. Two sequential methanol triturations are highly effective in producing purified PPPBP having a PP content below about 200 ppm.

Examples 1C, 1D, 2B, and 3B

The precipitation procedure of Example 1 and the trituration procedures of Examples 2 and 3 were repeated using a semicrude PPPBP containing 0.5378 wt. % of PP. In Example 1C, the precipitation procedure of Example 1 was followed, except that the pH of the solution was adjusted to about 3 to 4. In Example 1D, the precipitation procedure of Example 1 was followed, with the pH of the solution being adjusted to 9.5. In Example 2B, the product of Example 1D (precipitation at pH of 9.5) was purified using the single trituration procedure of Example 2. In Example 3B, the product of Example 1D (precipitation at pH of 9.5) was purified using the double trituration procedure of Example 3.

The wt. % of PP, percent purity of the PPPBP, and the yield for each Example is shown in Table 3. The percent yield is based on the weight of semicrude PPPBP.

TABLE 3

| Ex. | Stage | % Purity of PPPBP | % PP | % Yield |
|---|---|---|---|---|
| — | Semicrude PPPBP | | 0.5378 | |
| 1C* | After precipitation at pH = 3-4 | | 0.5310 | 98% |
| 1D | After precipitation at pH = 9.5 | 99.785 | 0.0786 | 97% |
| 2B | After precipitation at pH = 9.5 and one MeOH trituration | 99.926 | 0.0099 | 93.8% |
| 3B | After precipitation at pH = 9.5 and two MeOH triturations | 99.955 | 0.0011 | 91.9% |

*Control

As can be seen from the results shown in Table 3, aqueous methanol trituration can be used to remove PP from semicrude PPPBP containing high amounts of PP. Two sequential methanol triturations are highly effective to produce purified PPPBB having a PP content below about 50 ppm.

Example 6

The purified PPPBP of Example 4 and Example 5 were used to prepare copolymers of PPPBP and bisphenol A using an interfacial process.

The reaction setup consisted of 4-necked, round bottom flask fitted with two dropping funnels and a mechanical stirrer. The flask was charged with BPA and PPPBP monomers in the amounts shown in Table 4, water (100 mL), dichloromethane (100 mL), and the phase transfer catalyst. The contents were stirred under nitrogen blanket. To this stirred slurry, a solution of triphosgene in dichloromethane and an aqueous sodium hydroxide solution were added dropwise through separate dropping funnels. A sufficient amount of sodium hydroxide was added to maintain pH at 5 to 6. After stirring for another 30 minutes, the pH was raised to 10 to 11 by the addition of aqueous sodium hydroxide, to consume excess triphosgene. To this slurry, triethylamine and p-cumyl phenol were added and pH was again raised to about 12 by the addition of aqueous sodium hydroxide. Stirring was continued for another 10 minutes. Completion of reaction was inferred by increase of viscosity of the slurry. The dichloromethane layer was then thoroughly washed with dilute HCl, followed by washing with water. The polymer was obtained by the addition of sufficient methanol to the dichloromethane solution with stirring, filtration of the solid, and drying at 110° C.

TABLE 4

| Component | Mol. Wt. | Wt. added | Amount | Molar ratio |
|---|---|---|---|---|
| PPPBP | 391 | 11.73 g | 0.03 moles | 3 |
| BPA | 228.28 | 15.97 g | 0.07 moles | 7 |
| Triphosgene | | 16.75 g | | |
| NaOH | 40 | 15 g | 30% solution (w/v) | |
| Triethylamine | | | 200 µL | |
| p-cumyl phenol | | | 450 mg | |
| HCl | | | 1% soln | |

Short- and long-term heat aging stability of the two polymers was then determined. The color stability and heat aging results are summarized in Tables 5 and 6.

TABLE 5

| Source of PPPBP | PP content of the polymer (ppm)[1] | Short-term Heat Aging Stability (340° C., 5 minutes) | | | | | |
|---|---|---|---|---|---|---|---|
| | | Initial | | | After Heating | | |
| | | YI | Mn | Mw | YI | Mn | Mw |
| Ex. 4 | N.D. | 4 | 12987 | 32100 | 13 | 8925 | 19020 |
| Ex. 5 | 82 | 5 | 10823 | 29422 | 69 | 5158 | 10823 |

[1]Calculated based on the PP content of the PPPBP monomer

The data in Table 5 demonstrate an unexpected improvement in the short-term heat aging properties of copolymers produced using the purified PPPBP of Example 4. In particular, the color change in heat aged samples (340° C., 5 minutes) is significantly lower. Further, the percent decrease in the Mn and Mw (31% and 41%, respectively) of copolymers made using the PPPBP of Example 4 is significantly smaller than the decrease in Mn and Mw (52% and 63%, respectively) of copolymers made using the PPPBP of the prior art (Example 5).

TABLE 6

| Source of PPPBP | PP (ppm)[1] | Long-term Heat Aging Stability (7 days) | | | | | |
|---|---|---|---|---|---|---|---|
| | | Initial | | 160° C. | | 180° C. | |
| | | Mn | Mw | Mn | Mw | Mn | Mw |
| Ex. 4 | N.D. | 11201 | 28855 | 7373 | 14527 | 1333 | 9096 |
| Ex. 5 | 82 | 6640 | 13471 | 544 | 1274 | 194 | 266 |

[1]Calculated based on the PP content of the PPPBP monomer

The data in Table 6 demonstrates an unexpected degree of improvement in the properties of copolymers produced using the purified PPPBP of Example 4. In particular, after heat aging at 160° C. and 180° C., the percent decrease in Mn (34% and 88%, respectively) of copolymers made using the PPPBP of Example 4 is significantly smaller than the decrease in the Mw (92% and 97%, respectively) of copolymers made using the PPPBP of the prior art (Example 5). Similarly, after heat aging at 160° C. and 180° C., the percent decrease in Mw (50% and 68%, respectively) of copolymers made using the PPPBP of Example 4 is significantly smaller than the decrease in the Mw (91% and 98%, respectively) of copolymers made using the PPPBP of the prior art (Example 5).

For the purposes of this disclosure, the term "hydrocarbyl" is defined herein as a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; arylalkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl' as used herein refers to various forms of aryl groups that have been described hereinabove for the "hydrocarbyl" group.

The terms "comprising" (and its grammatical variations) as used herein is used in the inclusive sense of "having" or "including" and not in the exclusive sense of "consisting only of". The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

While the disclosure has been described with reference to a preferred embodiment, it will be understood by those skilled in the art that various changes can be made and equivalents can be substituted for elements thereof without departing from the scope of the disclosure. In addition, many modifications can be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

The invention claimed is:

1. A method for producing a purified 2-aryl-3,3-bis(4-hydroxyaryl)phthalimidine of formula (I)

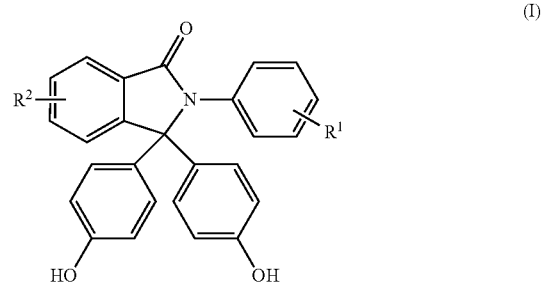

(I)

wherein $R^1$ is hydrogen or a $C_{1-25}$ hydrocarbyl group and $R^2$ is hydrogen, a $C_{1-25}$ hydrocarbyl group, or a halogen, and wherein the method comprises:
heating a reaction mixture comprising
a phenolphthalein compound of formula (II)

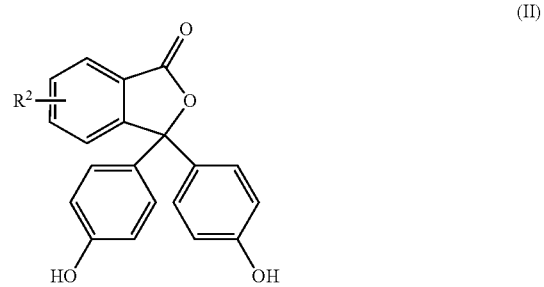

(II)

wherein $R^2$ is hydrogen, a $C_{1-25}$ hydrocarbyl group, or a halogen,
a primary aryl amine of formula (III),

(III)

wherein $R^1$ is hydrogen or a $C_{1-25}$ hydrocarbyl group, and
an acid catalyst, to form a phthalimidine compound of formula (I);
precipitating the phthalimidine compound from the reaction mixture to provide a crude phthalimidine compound;
dissolving the crude phthalimidine compound in an aqueous base solution;
precipitating the dissolved, crude phthalimidine compound from the aqueous base solution by adding an acid in an amount effective to lower the pH of the solution to 1.0 to less than 9.0, to provide a semicrude phthalimidine compound;
isolating the semicrude phthalimidine compound from the aqueous base solution, to provide the 2-aryl-3,3-bis(4-hydroxyaryl)phthalimidine of formula (I); and
sequentially triturating the purified phthalimidine of formula (I) at least twice with an aqueous methanol solution to provide a highly purified 2-aryl-3,3-bis(4-hydroxyaryl) phthalimidine of formula (I), having a phenolphthalein compound content of less than 200 ppm, based on the weight of the 2-aryl-3,3-bis(4-hydroxyaryl)phthalimidine.

2. A highly purified 2-aryl-3,3-bis(4-hydroxyaryl)phthalimidine produced by the method of claim 1.

3. A 2-aryl-3,3-bis(4-hydroxyaryl)phthalimidine of formula (I)

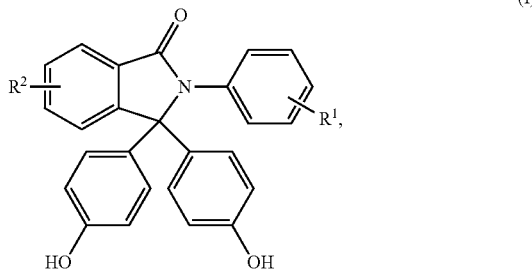

(I)

wherein $R^1$ is hydrogen or a $C_{1-25}$ hydrocarbyl group and $R^2$ is hydrogen, a $C_{1-25}$ hydrocarbyl group, or a halogen, and comprising 200 ppm or less of a phenolphthalein compound of formula (II)

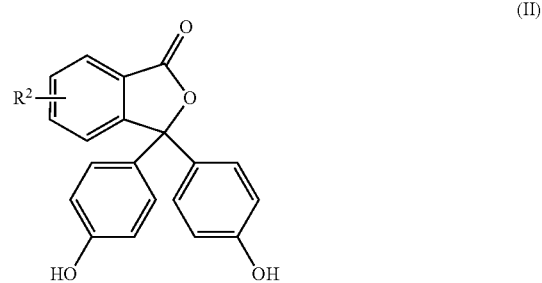

(II)

wherein $R^2$ is hydrogen, a $C_{1-25}$ hydrocarbyl group, or a halogen.

4. The 2-aryl-3,3-bis(4-hydroxyaryl)phthalimidine of claim 3, comprising 100 ppm or less of a phenolphthalein compound of formula (II).

5. The 2-aryl-3,3-bis(4-hydroxyaryl)phthalimidine of claim 3, comprising 50 ppm or less of a phenolphthalein compound of formula (II).

6. A polymer comprising structural units derived from the 2-aryl-3,3-bis(4-hydroxyaryl) phthalimidine of claim 3.

7. A polymer comprising structural units derived from 2-aryl-3,3-bis(4-hydroxyaryl) phthalimidine compound of claim 4.

8. A polymer comprising structural units derived from 2-aryl-3,3-bis(4-hydroxyaryl) phthalimidine compound of claim 5.

9. The polymer of claim 8, wherein the polymer is a polycarbonate copolymer comprising units derived from the 2-aryl-3,3-bis(4-hydroxyaryl)phthalimidine compound of claim 5 and units derived from bisphenol A.

* * * * *